United States Patent
Keating

(10) Patent No.: US 11,986,363 B2
(45) Date of Patent: May 21, 2024

(54) REAL TIME ANATOMICAL ADAPTATION

(71) Applicant: Global Dental Sciences, LLC, Scottsdale, AZ (US)

(72) Inventor: Scott C. Keating, Louisville, CO (US)

(73) Assignee: Global Dental Science, LLC, Scottsdale, AZ (US)

(*) Notice: Subject to any disclaimer, the term of this patent is extended or adjusted under 35 U.S.C. 154(b) by 645 days.

(21) Appl. No.: 16/278,591

(22) Filed: Feb. 18, 2019

(65) Prior Publication Data
US 2019/0254786 A1    Aug. 22, 2019

Related U.S. Application Data

(60) Provisional application No. 62/631,609, filed on Feb. 16, 2018.

(51) Int. Cl.
*A61C 13/00* (2006.01)
*A61C 9/00* (2006.01)
*G16H 10/60* (2018.01)

(52) U.S. Cl.
CPC ........ *A61C 13/0004* (2013.01); *A61C 9/0053* (2013.01); *G16H 10/60* (2018.01)

(58) Field of Classification Search
CPC ... A61C 13/0004; A61C 9/0053; G16H 10/60
See application file for complete search history.

(56) References Cited

U.S. PATENT DOCUMENTS

| | | | |
|---|---|---|---|
| 6,318,994 B1* | 11/2001 | Chishti | A61C 7/00 433/24 |
| 7,245,977 B1* | 7/2007 | Simkins | A61C 7/00 700/98 |
| 8,100,692 B2 | 1/2012 | Diangelo | |
| 9,717,570 B2 | 8/2017 | Chung et al. | |
| 9,775,688 B2 | 10/2017 | Herweg | |
| 10,022,916 B2 | 7/2018 | Powell | |
| 10,159,545 B2 | 12/2018 | Thome | |
| 2002/0042038 A1* | 4/2002 | Miller | A61C 7/00 433/24 |
| 2002/0064748 A1* | 5/2002 | Chishti | G06F 30/20 433/24 |
| 2003/0129565 A1* | 7/2003 | Kaza | A61C 7/002 433/213 |

(Continued)

FOREIGN PATENT DOCUMENTS

| DE | 102006023673 | 11/2007 |
|---|---|---|
| EP | 1798459 | 6/2007 |

(Continued)

OTHER PUBLICATIONS

EP Application 18161215.1—EP Search Report dated Jun. 5, 2018.

(Continued)

*Primary Examiner* — Nicholas D Lucchesi
(74) *Attorney, Agent, or Firm* — Derrick Harvey

(57) ABSTRACT

The invention comprises an improved method and system for building a denture. The invention further comprises a technique for building teeth and a denture base in a digital space. The invention even further comprises a method for adapting a digital denture base contemporaneously with changes made to digital teeth on the same model.

12 Claims, 8 Drawing Sheets

(56) References Cited

U.S. PATENT DOCUMENTS

| | | | |
|---|---|---|---|
| 2008/0199827 A1* | 8/2008 | Kamer | A61C 13/0004 433/75 |
| 2009/0220916 A1 | 9/2009 | Fisker | |
| 2010/0151404 A1* | 6/2010 | Wu | A61C 9/0053 433/24 |
| 2013/0101962 A1 | 4/2013 | Howe | |
| 2013/0216323 A1 | 8/2013 | Matthias et al. | |
| 2014/0087327 A1 | 3/2014 | Noack | |
| 2014/0255873 A1 | 9/2014 | Bullis et al. | |
| 2014/0272796 A1 | 9/2014 | Grobbee et al. | |
| 2015/0064653 A1 | 3/2015 | Grobbee et al. | |
| 2015/0111177 A1* | 4/2015 | Fisker | A61C 13/08 433/196 |
| 2015/0182314 A1 | 7/2015 | Morales et al. | |
| 2015/0251359 A1 | 9/2015 | Powell | |
| 2016/0317263 A9 | 11/2016 | Morales et al. | |
| 2017/0071706 A1* | 3/2017 | Lee | A61C 13/0004 |
| 2017/0128161 A1 | 5/2017 | See et al. | |
| 2018/0147032 A1 | 5/2018 | Keating | |
| 2018/0257187 A1 | 9/2018 | Grobbee | |
| 2019/0053881 A1 | 2/2019 | Grobbee et al. | |
| 2019/0083205 A1 | 3/2019 | Van Der Meer | |
| 2019/0117350 A1* | 4/2019 | Christian | A61C 9/004 |

FOREIGN PATENT DOCUMENTS

| | | |
|---|---|---|
| EP | 2403427 | 1/2012 |
| EP | 3216420 | 9/2017 |
| EP | 3284438 | 2/2018 |
| WO | 2010094922 | 8/2010 |

OTHER PUBLICATIONS

EP Applicaiton 18189345—EP Search Report dated Jan. 16, 2019.
EP Application 17192480—EP Search Report Apr. 11, 218.
U.S. Appl. No. 15/711,857—Restriction Requirement dated Nov. 29, 2018.
U.S. Appl. No. 15/711,857—Non-Final Office Action dated May 15, 2019.
U.S. Appl. No. 15/711,857—Final Office Action dated Feb. 19, 2020.
U.S. Appl. No. 15/823,379—Non-Final Office Action dated Jan. 27, 2020.

* cited by examiner

REAL TIME ANATOMICAL ADAPTATION

RELATED APPLICATIONS

This application claims priority from U.S. Provisional Application No. 62/631,609 filed on Feb. 16, 2018 and entitled "Real Time Anatomical Adaptation," the entire contents of which are hereby fully incorporated herein.

BACKGROUND OF THE INVENTION

The invention relates to an improved method and system for building a denture. The invention further relates to a technique for building, adaptation and teeth in a digital space. The invention even further relates to a method for auto-sizing arches of a digital denture contemporaneously with changes made to digital teeth on the same model. The invention even further relates to a method for maintaining anatomical relationships in teeth while changing the arch.

1. FIELD OF THE INVENTION

The present invention relates to the field of manufacturing digital dentures. The present invention further relates to designing digital dentures for patients. The present invention even further relates to a system of modifying digital denture teeth while, in real time, adapting the arches of the denture through computer software. The present invention even more particularly relates to maintaining anatomical relationships between teeth while changing arches of the digital prosthetic design.

2. DESCRIPTION OF RELATED ART

The idea of designing teeth in virtual space is fairly common in prior art. For prosthetic solutions such as dentures and crown/bridge work, such solutions are well known in the prior art and are well commercialized. Changes in the arch can cause overjet or tooth interferences. Teeth are designed and customized for each patient by using data derived from imaging the patient's anatomy, occlusion, existing prosthetics, etc. However, changing tooth size, position, or angle can affect arch length so that the tooth spacing and occlusion with antagonist teeth are adversely impacted is accomplished manually in the design phase, or requires that the prosthetic device must undergo grinding once it is manufactured.

There remains a solution for a method and system for improving the process of digitally correcting the arches and teeth spacing of a dental prosthetic during the process of overall changes to artificial teeth designed in a computer software program. There further remains a solution for occlusal adaptation tool disposed within prosthetic tooth design software that enables real-time adjustments upon the arches of the prosthetic and the spaces between the teeth as they affect overall occlusion and tooth spacing/interferences. There even further remains a solution that eliminates the need to address or correct functional occlusion for the same patient upon subsequent re-workings of the same prosthesis. There remains a need for a solution that produces prosthetic teeth set up that may be manufactured without subsequently undergoing additional grinding or other reductive modification.

SUMMARY OF THE INVENTION

These and other objects were met with the present invention. The present invention provides a method for designing a prosthetic structure including an upper and/or lower arch, the method comprising:

acquiring either data relevant to the natural anatomy of a patient or a prosthetic outcome to be built for the patient, building or modifying a prosthetic tooth structure having an upper arch and/or a lower arch a computer software program, the upper arch and/or lower arch having an upper arch tooth anatomy and/or a lower arch tooth anatomy, and automatically adapting one of the upper and/or lower arch and the upper arch tooth anatomy and/or lower arch tooth anatomy to maintain an anatomical occlusion between the upper arch tooth anatomy and/or lower arch tooth anatomy so that tooth interferences created by changes in arches are corrected and that tooth gaps that are undesired are closed.

In another embodiment, the present invention may comprise a method for maintaining tooth space between digitally designed teeth, the method comprising a method for maintaining anatomical relationships between teeth while designing or modifying the digital prosthetic upper and lower arches, the method comprising the following steps: adapting or modifying a prosthetic tooth structure in a computer software program in reaction to modification of the upper and/or lower prosthesis archforms; adapting the occlusal and interproximal tooth surfaces of adjacent teeth to maintain proper anatomical relationships, from mesial/distal translation due to design or modification of the upper or lower arch forms; adapting the occlusal and interproximal tooth surfaces of antagonist teeth to maintain proper anatomical relationships due to coronal/apical translation; adapting the occlusal and interproximal tooth surfaces of antagonist teeth to maintain proper anatomical relationships due to buccal/lingual translation; adapting the occlusal and interproximal tooth surfaces of antagonist and adjacent teeth to maintain proper anatomical relationships due to mesial/distal rotation (tilt); adapting the occlusal and interproximal tooth surfaces of antagonist and adjacent teeth to maintain proper anatomical relationships due to buccal/lingual rotation (tilt); adapting the occlusal and interproximal tooth surfaces of antagonist and adjacent teeth to maintain proper anatomical relationships due to flare rotation, wherein the steps in the method have the effect of automatically correcting improper relationships of teeth or malocclusion so that, in response to any changes made by the user to the design of the digital prosthesis, such changes resulting in maintaining a proper anatomical relationship of the upper arch teeth and the lower arch teeth.

BRIEF DESCRIPTION OF THE DRAWINGS

A more complete understanding of the present invention may be derived by referring to the detailed description and claims when considered in connection with the Figures, where like reference numbers refer to similar elements throughout the Figures:

DETAILED DESCRIPTION OF THE INVENTION

Figure 1A:
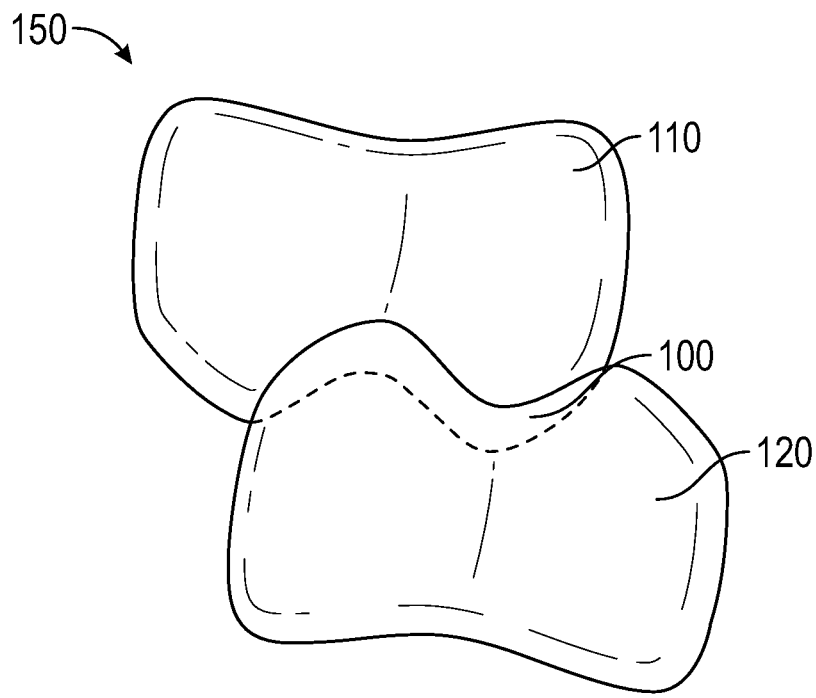
FIG. 1a depicts a side view of a representative upper tooth and lower tooth having an interference as a result of a digital software modification.

The present invention solves a number of issues with designing prosthetic teeth in the prior art. The present invention provides a digital adaptation of the upper arch teeth and/or lower arch teeth during the process of modifying the one or more of the teeth or arches. The present invention reduces the need to manually correct the digital prosthetic due to cross-bite disruption, overjet of the upper arch teeth, interferences including interpenetration, or over spacing of between the tooth or teeth portions. The invention further solves the practice of reducing teeth that could also reduce important enamel layer. The invention further solves the issue of reduced spacing in cases such as in case of an implant bar resulting in reduced vertical dimension between the edentulous ridges, on either or both sides.

According to the illustrations provided, a method and system of adapting the anatomical occlusion to movements and modifications of the teeth are disclosed.

In an embodiment of the inventive process, a user who designs a dental prosthetic structure may engage a digital software platform that utilizes patient information and data acquired through imaging, impressions and scans thereof, and other means known in the arts. In one embodiment of the invention, the user may engage in standalone computation that is unique to the patient information. In another embodiment, the user may select a template from a database of selected anatomical profiles, or of preferred dental prostheses that provide a setup and analogue to sculpt the customized prosthesis for the patient which ultimately be manufactured through milling or other reductive processes, or by additive processes such as 3D printing, or by other methods known in the arts to convert digital prosthetic devices into real world physical structures.

The user may begin sculpting the teeth, according to techniques and tools utilized in the software displayed in a computer interface. In a preferred embodiment of the invention, during modification of the upper arch and its teeth and/or lower arch and its teeth a number of undesirable anatomical relationships may result from such changes. Such prosthetic structures may be displayed in a direct or exploded view under the tooth portion of the prosthetic structure, for example on a display screen or other 3D interface to the user such as a hologram.

In a first embodiment, a user may create or utilize existing profiles to modifies a teeth set up in a designing operation of the software. To correct malocclusion profiles as seen in the illustrations and as generally known in the arts, the user will often modify the arches, having a direct effect on the teeth on the affected portions of the upper arch and lower arch of the prosthetic. Such changes in the arch that would otherwise introduce diastemas (such as in the lower canine and bicuspids) may be correlated to automatic corrections by auto-sizing the arches to close the diastemas. In an embodiment of the invention, the occlusal ramps of the antagonist teeth may be maintained in contact, so that such teeth stay in occlusion during the changes in the arch and other resulting changes of the other teeth. Other changes to the arch may create undesired anatomical relationships with the teeth that the present invention may correct in real time, or in rapid succession as described further infra. In other embodiments, sections of the teeth or even isolated teeth may be designed to accommodate partial prosthetic tooth solutions.

In a second embodiment of the invention, the user may implement a variety of changes, from subtle sculpting to remove interproximal interferences or overpenetration into the occlusal plane of the upper arch teeth and lower arch teeth. The user may set interproximal spacing rules between teeth, so that a minimum spacing between teeth is achieved for functional anatomical occlusion, or even set an aesthetically driven spacing so that a diastema is maintained or created in the front central teeth. According to the embodiments of the invention, the inventive method and software tool operates by morphing teeth in different directions, maintaining relationship between adjacent teeth, opposing teeth, having balanced occlusion, utilizing canine guidance, as a result of algorithms that affect the overall upper arch teeth and lower arch teeth as design changes are made on the screen.

In another embodiment of the invention, the process and software tool enable the adaptation of the teeth as a result of changes in arch shape and size rather than by scaling teeth.

Other variations and specialized circumstances may be implemented with this inventive base adaptation.

Figure 1B:
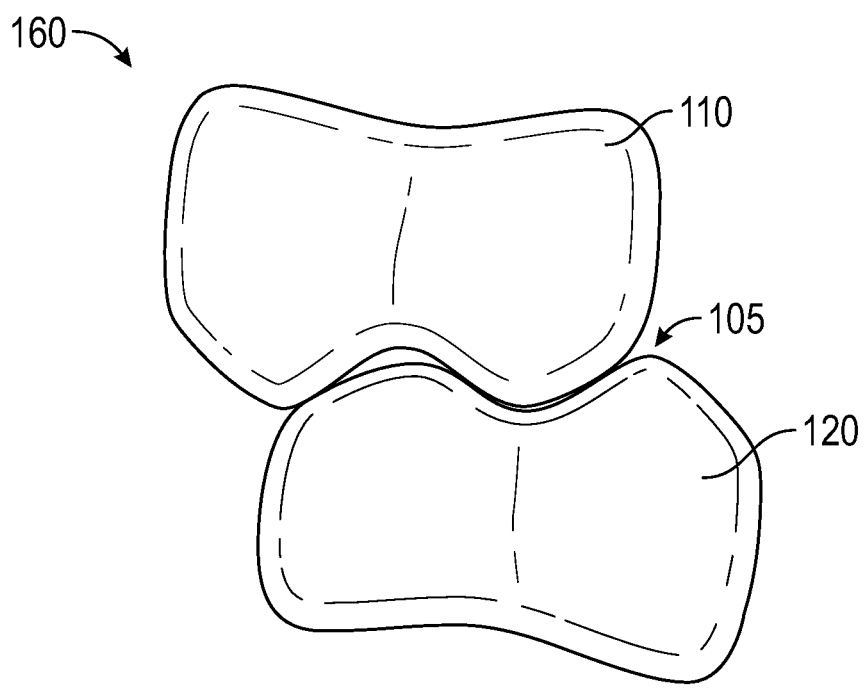
FIG. 1b illustrates the same teeth from FIG. 1a having been corrected to a functional anatomical occlusion according to an embodiment of the invention.

As the digital design software sets teeth upon a patient's arch, an initial configuration 150 may result in the virtual interference 100 as illustrated by misalignment of the peaks of the cusps of the teeth into the fossa(e) of the upper tooth 110 and lower tooth 120. In the inventive embodiment depicted in FIG. 1b, a morphological adaptation of the upper and/or lower teeth may correct the virtual interference so that upper tooth 110 and lower tooth 120 are brought into a relationship of anatomical occlusion.

Figure 2A:
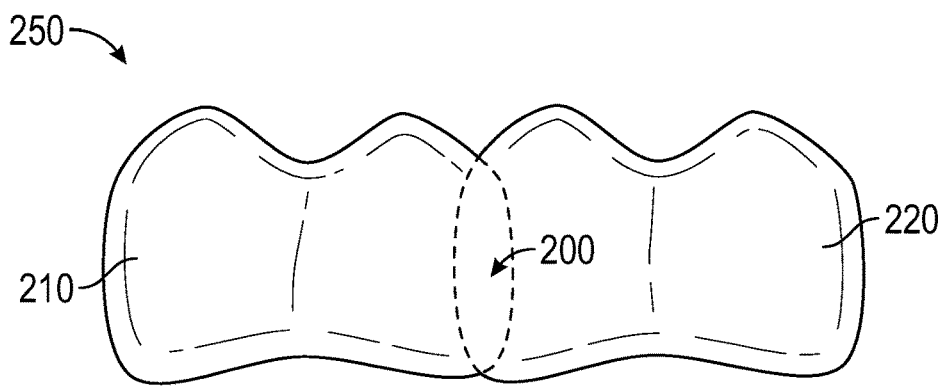
FIG. 2a illustrates a side view of two lower arch teeth having an interference as a result of a digital software set-up configuration.
Figure 2B:
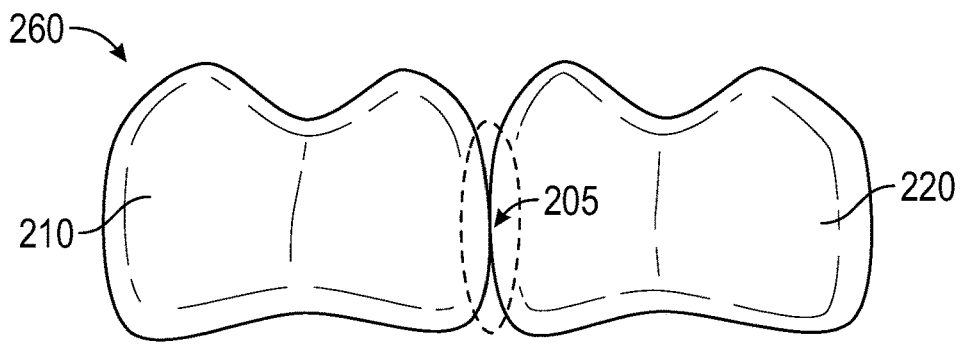
FIG. 2b illustrates the same lower teeth having been corrected to anatomical interproximal occlusion according to an embodiment of the invention.

In another embodiment of the invention, FIG. 2a shows the result of an initial configuration 250 that results in a virtual interference 200 of a first lower tooth 210 and an adjacent lower tooth 220 having an interproximal interpenetration of the first lower tooth 210 and the adjacent lower tooth 220. FIG. 2b illustrates a morphological adaptation 260 of the first lower tooth 210 and the second lower tooth 220, correcting the virtual interference so that the first lower tooth 210 and the adjacent lower tooth 220 are brought into a relationship of anatomical interproximal occlusion 205.

Figure 3:
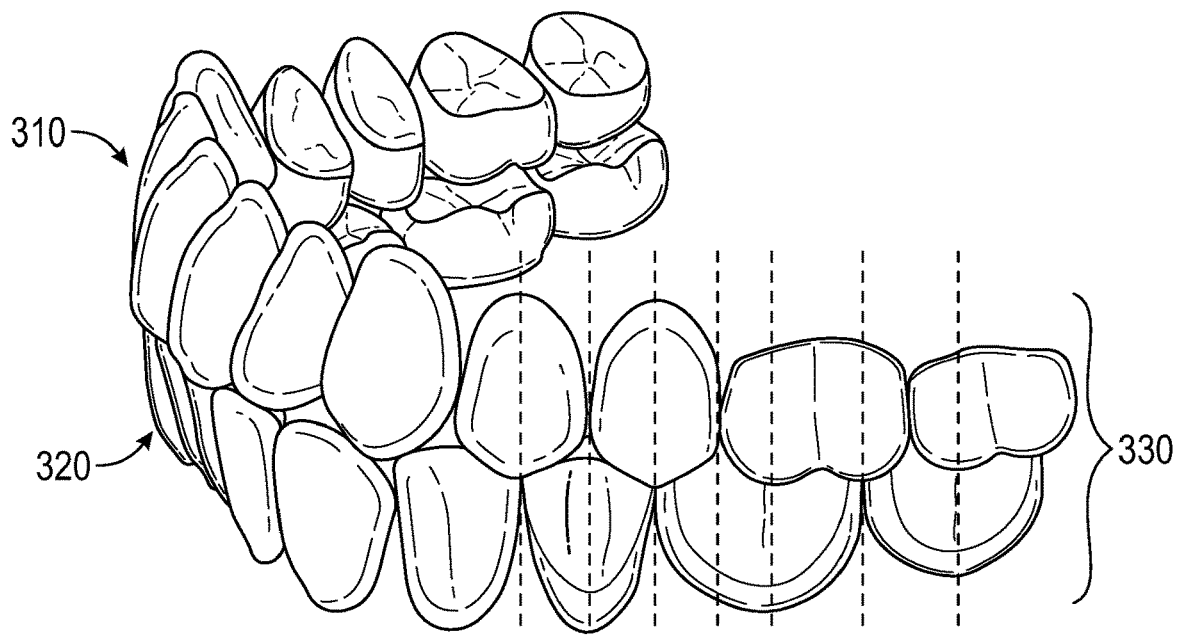
FIG. 3 depicts a side perspective view of upper arch teeth and lower arch teeth being set to a functional anatomical occlusion.

FIG. 3 shows a baseline of proper setup 310 of an upper arch 310 and a lower arch 320 that may be used as reference point for the inventive method in applying corrections to misalignment of teeth in a digital design software application as technicians and designer seek to incrementally apply changes to the proper set-up.

Figure 4A:
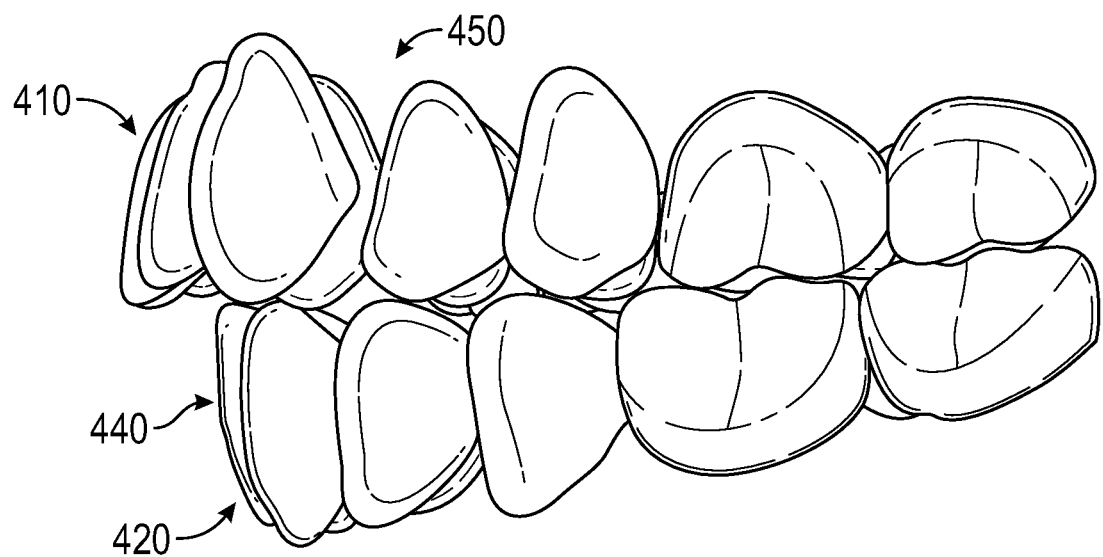
FIG. 4a shows a side perspective view of an overjet modification and resulting malocclusion in the absence of the inventive application in lower arch teeth.
Figure 4B:
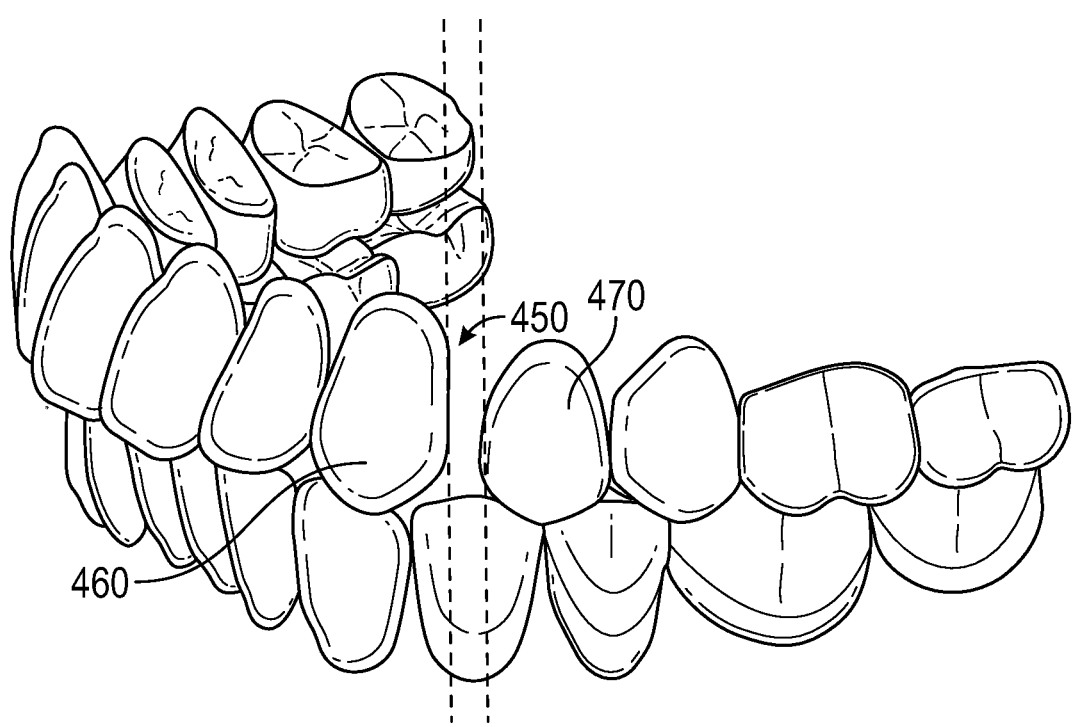
FIG. 4b shows a side perspective view of the same upper arch teeth and lower arch teeth from FIG. 4a with a resulting diastema between upper arch teeth.

Looking now to FIG. 4a and FIG. 4b, in absence of the inventive technology, one may see the problems of a physical or software set-up. Here, a correction 440 in FIG. 4a shows the result of a digital technician increasing the overjet (for anterior functional reasons) to correct a hypothetically protruding lower jaw, and thus pushing the lower anterior teeth 420 as well as the upper anterior teeth 410 which are following to maintain occlusion with the lowers, thus creating a diastema 450 between the first canine 460 of the upper canines and the first upper pre-molars 470 shown in FIG. 4b.

Figure 5A:
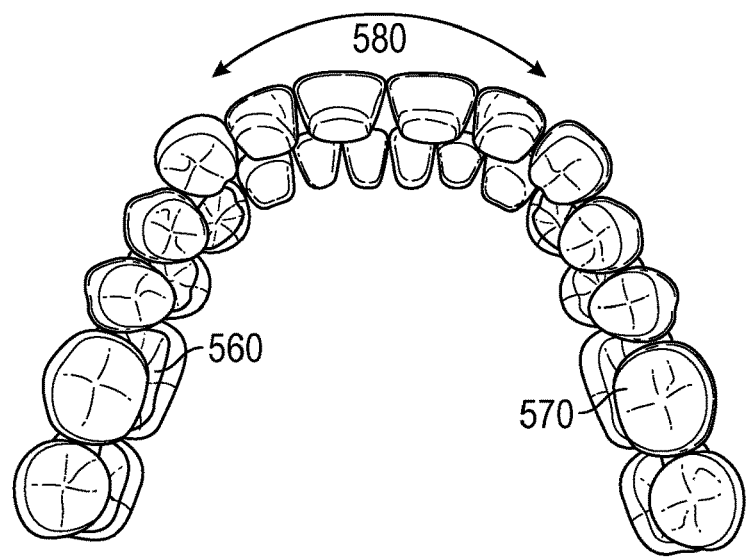
FIG. 5a depicts a top plan view of the upper and lower teeth being adapted to close a diastema as seen in FIGS. 4a and 4b, according to an embodiment of the invention.

In an embodiment of the invention, FIG. 5a shows an adaptation of the lower anterior teeth so that they are evenly spaced to correct the undesired interproximal space (or diastema) 450 shown in FIG. 4a and FIG. 4b. As the arch distribution 580 indicates in FIG. 5a, adaptations in size and shape may account for the morphological changes in this inventive concept that result in now-even distribution of teeth along the lower arch 560 to close the diastema and bring about functional anatomical occlusion with regard to the upper arch 570 to lower arch 560.

Figure 5B:
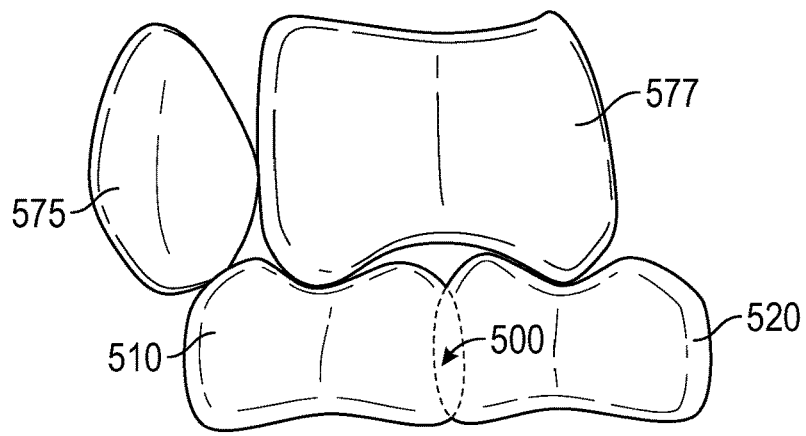
FIG. 5b depicts side perspective view of a pair of upper teeth opposing a pair of lower teeth having the interproximal interference created by closing the diastema in FIGS. 4a and 4b, as being brought to occlusion according to an embodiment of the invention.
Figure 5C:
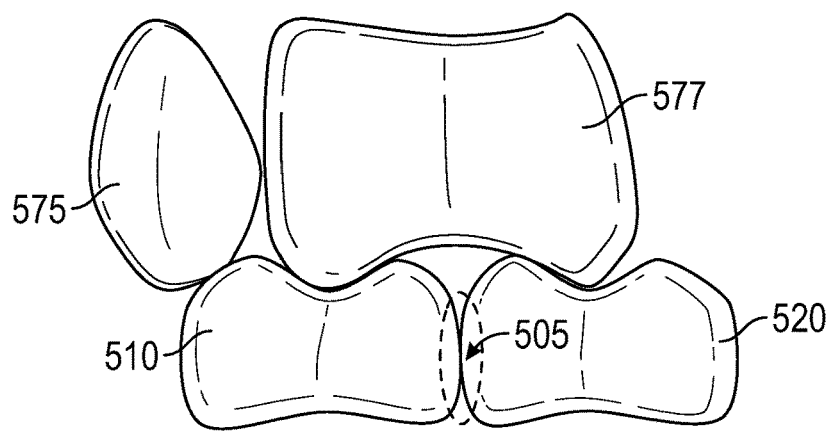
FIG. 5c depicts a side perspective view of an pair of upper teeth opposing a pair of lower teeth resulting from the inventive method applied to correct undesired interproximal spacing as illustrated in FIGS. 4a and 4b.
Figure 5D:
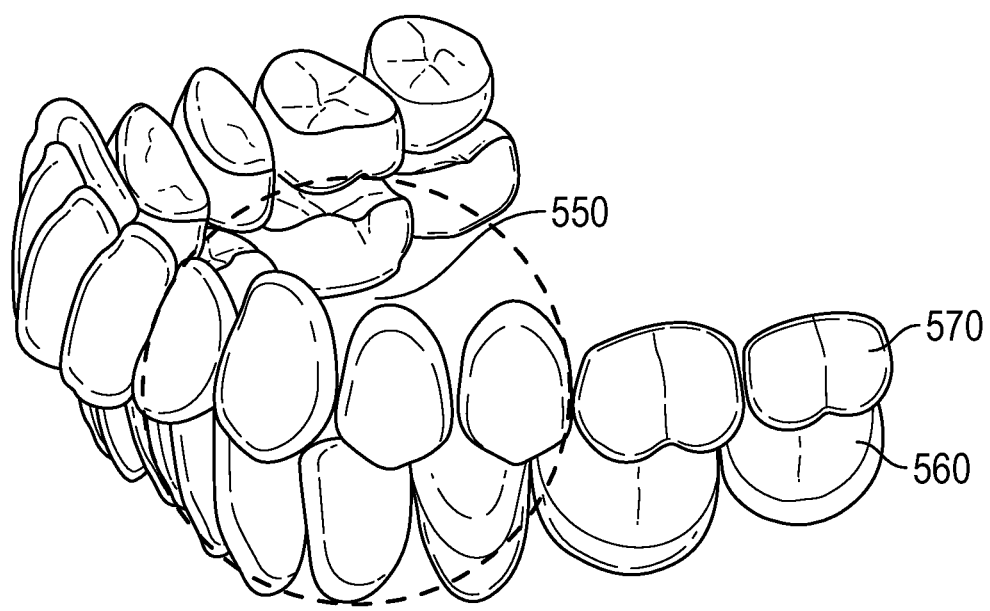
FIG. 5d depicts a side perspective view of an upper arch of teeth and lower arch of teeth resulting from the inventive method applied to correct undesired interproximal spaces as illustrated in FIGS. 4a and 4b.

In ensuring that while a technician is digitally applying corrections issues such as increasing an overjet to address a protruding lower jaw, and ensuring that the diastema in FIGS. 4a and 4b do not develop during such correction, the movement of one or more of the arches can create yet other issues with occlusion such as interproximal interferences as illustrated in FIGS. 5b and 5c. In an aspect of the invention, lower teeth 510 and 520 may adapt while maintaining occlusion with opposing upper teeth 575 and 577, respectively, to ensure interproximal occlusion during the technician's digital corrections of interproximal interferences. Thus, in FIG. 5d, the inventive process has ensured that while a technician corrects the protruding lower jaw in FIG. 4a, that the teeth in the upper and lower arch are automatically adapting to the movements of the other teeth or groups of teeth so that the functional anatomical occlusion is automatically achieved.

Figure 6A:
FIG. 6a depicts a side perspective view of a lower ridge and upper ridge having space limitations in their vertical relationship.
Figure 6B:
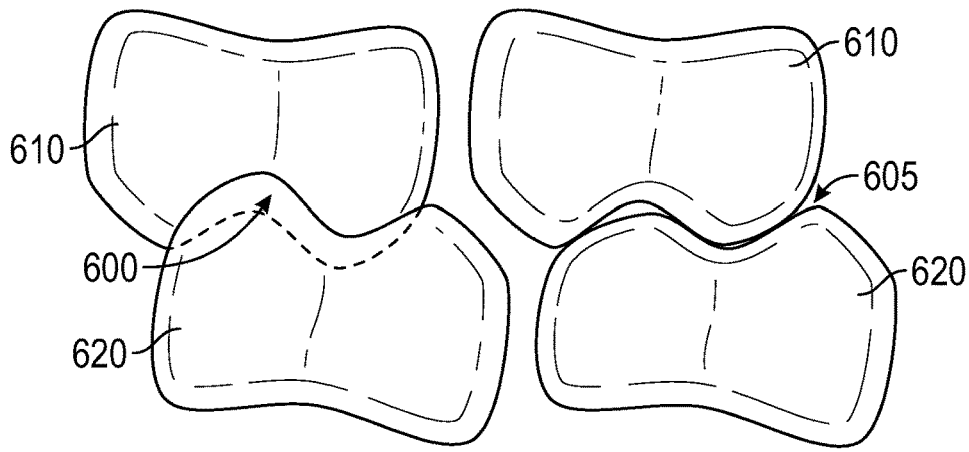
FIG. 6b depicts modifying interpenetration interference between an upper arch tooth into a lower arch tooth and then the same upper and lower arch teeth having an embodiment of the inventive method applied to correct the interpenetration interference and maintain an anatomical relationship and occlusion.
Figure 6C:
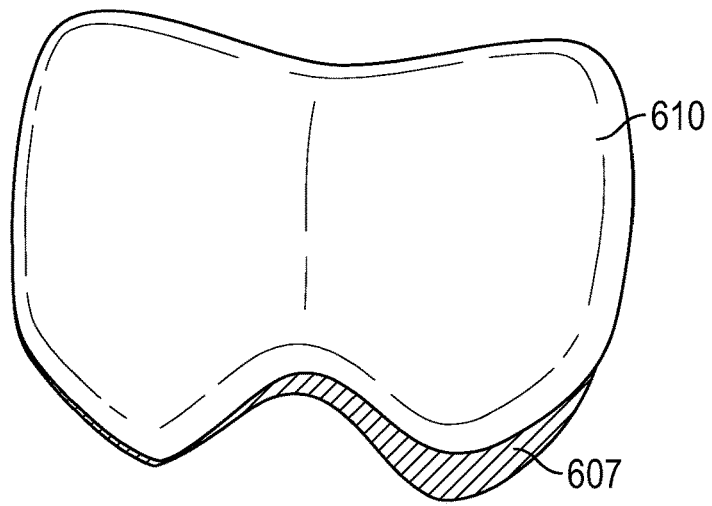
FIG. 6c illustrates the how the upper tooth in FIG. 6b was adapted according to an embodiment of the invention to correct the interpenetration interference and maintain an anatomical relationship and occlusion.

FIG. 6a shows a scenario of diminished vertical spacing between upper arch 660 and lower arch 670. This scenario may be encountered due to a bar assembly used in the denture prosthetic, to high profile implants or anatomical constraints within the patient. In an exemplary illustration of how the inventive process may apply morphological adaptions when applying corrections to compromised vertical dimension, FIG. 6b first shows how the compaction of upper tooth 610 and opposing lower tooth 620 creates interference 600 in a typical operation in a digital design software when the operator/technician sets up teeth within reduced vertical dimension, then shows how the inventive process morphologically adapted the same upper tooth 610 and opposing lower tooth 620 to allow closing of the jaws within occlusion 605. This embodiment of the invention shows that the adaptation is not simply a scaling reduction of teeth or Boolean change in the upper tooth, to that point FIG. 6c highlights the adapted portion 607 of upper tooth 610 that brings upper tooth 610 and lower tooth 620 into occlusion. In other embodiments not shown, the tooth may be increased in volume in order to meet other misalignment issues, or even include both reductions and additions within the same tooth or teeth being morphologically adapted.

FIG. 7 illustrates a scenario where the upper and lower teeth have an ideal relationship in a nominal set-up, but that an unseen patient issue forces the designer in the digital software to move the teeth. For example, a misaligned left jaw on the patient could necessitate the need to move the upper arch teeth 775 on the left side bucally, and the lower arch teeth on the left side 765 lingually. In most digital design software programs, such movement would set the left arches into a cross-bite relationship as illustrated in 7b.

Figure 7A:
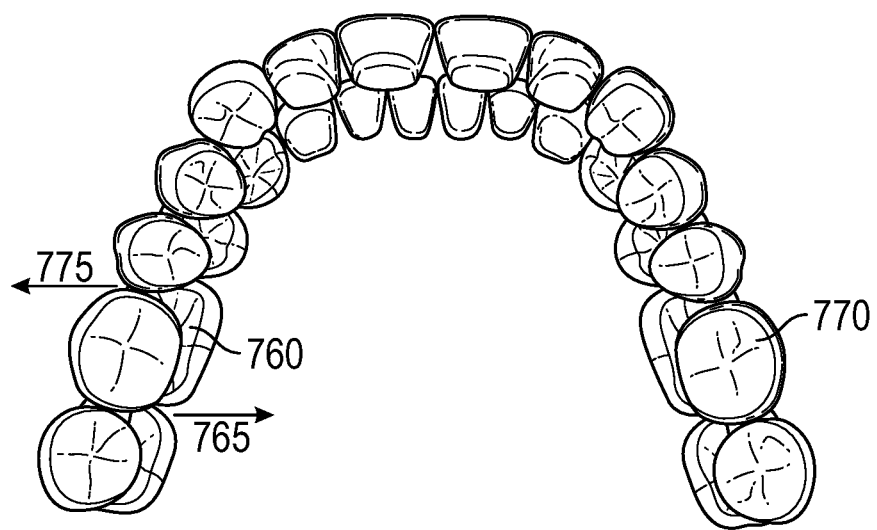
FIG. 7a illustrates a top perspective view of an upper arch being moved into cross bite relationship with a lower arch as a result of an arch modification to correct a jaw misalignment.
Figure 7B:
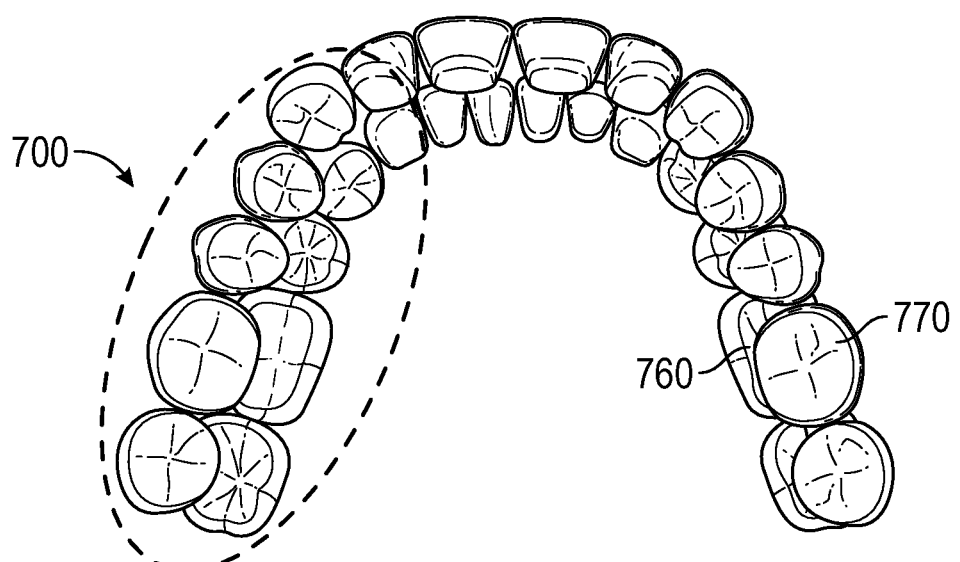
FIG. 7b illustrates a top perspective view of an upper arch in a cross bite relationship with a lower arch as a result of the arch modification as a result of an arch modification to correct a jaw misalignment.
Figure 8A:
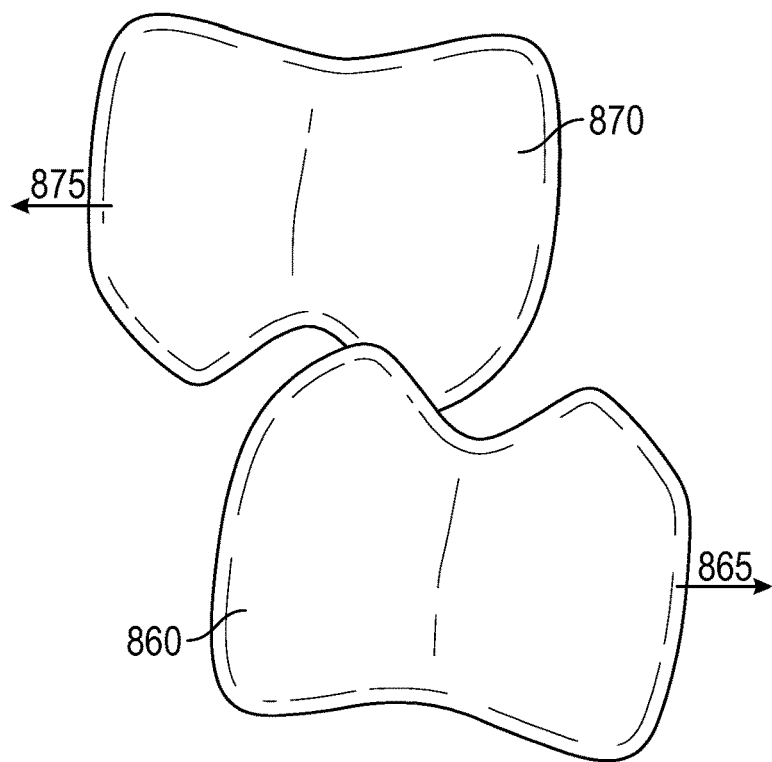
FIG. 8a depicts a side view of an upper arch tooth and a lower arch tooth in cross bite disruption as illustrated in FIG. 7b.
Figure 8B:
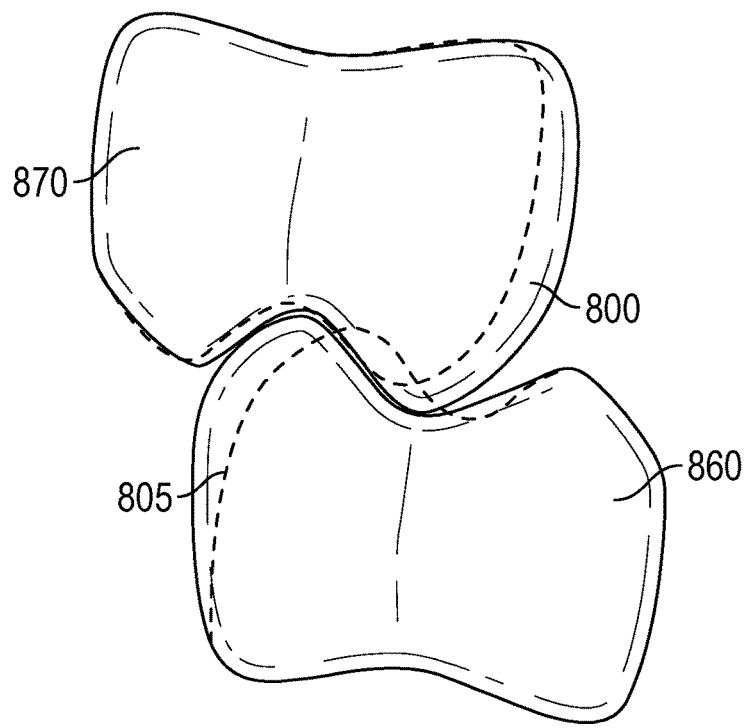
FIG. 8b depicts a side view of an upper arch tooth and a lower arch tooth in cross bite disruption being adapted into functional occlusion during the digital arch correction procedure according to embodiments of the invention.

FIG. 8 shows an embodiment of the invention that brings the cross-bite relationship shown in FIG. 7b back into occlusion while correcting for the misaligned jaw creating by moving the upper and lower arch teeth as indicated in FIG. 7a. FIG. 8a shows the virtual interference created in the cross-bite relationship described above and illustrated in FIG. 7b. FIG. 8b shows an embodiment of the invention that adapts an exemplary upper tooth and lower tooth to correct the cross-bite relationship during the tooth ridge movements indicated in FIG. 7a. In other embodiments of the invention, aging patients may present with bone resorption or other factors that necessitate tooth profiles that differ from their natural teeth, whereby an invention may morphologically change the tooth size, shape and or volume to restore a functional occlusion.

Other variations and specialized circumstances may be implemented with this inventive base adaptation.

While the present invention has been described in conjunction with the specific embodiments set forth above, many alternatives, modifications and other variations thereof will be apparent to those of ordinary skill in the art. All such alternatives, modifications and variations are intended to fall within the spirit and scope of the present invention.

What is claimed is:

1. A computer implemented method for maintaining anatomical relationships between teeth while designing or modifying digital prosthetic upper and lower arches, the method comprising the following steps:

Contemporaneously adapting or modifying a prosthetic tooth structures by a computer software program to maintain proper anatomical relationships between prosthetic tooth structures in upper and/or lower prosthetic archforms in reaction to modification of the upper and/or lower prosthesis archforms by a user, Contemporaneously adapting or modifying the occlusal and interproximal tooth surfaces of adjacent teeth to maintain proper anatomical relationships, from mesial/distal translation due to design or modification of an upper or lower arch forms by a user;

Contemporaneously adapting or modifying the occlusal and interproximal tooth surfaces of antagonist teeth to maintain proper anatomical relationships due to coronal/apical translation;

Contemporaneously adapting or modifying the occlusal and interproximal tooth surfaces of antagonist teeth to maintain proper anatomical relationships due to buccal/lingual translation;

Contemporaneously adapting or modifying the occlusal and interproximal tooth surfaces of antagonist and adjacent teeth to maintain proper anatomical relationships due to mesial/distal rotation/tilt;

Contemporaneously adapting or modifying the occlusal and interproximal tooth surfaces of antagonist and adjacent teeth to maintain proper anatomical relationships due to buccal/lingual rotation/tilt; and Contemporaneously adapting or modifying the occlusal and interproximal tooth surfaces of antagonist and adjacent teeth to maintain proper anatomical relationships due to flare rotation, wherein the steps in the recited method have the effect of the computer software program contemporaneously maintaining anatomical relationships of prosthetic tooth structures in upper and/or lower prosthetic archforms in response to any changes made by the user to the design of a digital prosthesis.

2. The method of claim 1, the step of contemporaneously adapting or modifying the occlusal and interproximal tooth surfaces of adjacent teeth to maintain proper anatomical relationships, from mesial/distal translation due to design or modification of the upper or lower arch forms including maintaining diastemata or conceding needed space.

3. The method of claim 1 further comprising that wherein the digital prosthetic upper and lower arches are set in anatomical occlusion prior to adaptation or modification in the recited steps.

4. The method of claim 1, the step of contemporaneously adapting or modifying a prosthetic tooth structure further comprising changes in arch shape and size rather than by scaling teeth.

5. The method of claim 1 further comprising morphing teeth in different directions.

6. The method of claim 1, the step of contemporaneously adapting or modifying a prosthetic tooth structure in a computer software program in reaction to modification of the upper and/or lower prosthesis archforms further utilizing canine guidance.

7. A method for designing a prosthetic structure including an upper and/or lower arch, the method comprising:

acquiring either data relevant to a natural anatomy of a patient or a prosthetic outcome to be built for the patient, building or modifying a prosthetic tooth structure having an upper arch and/or a lower arch with a computer software program, the upper arch and/or lower arch having an upper arch tooth anatomy and/or a lower arch tooth anatomy and being set in anatomical occlusion, and contemporaneously adapting one of the upper or lower arch and the upper arch tooth anatomy or lower arch tooth anatomy within the computer software program to maintain an anatomical occlusion between the upper arch tooth anatomy and/or lower arch tooth anatomy so that tooth interferences created by user-generated changes in arches are corrected and that tooth gaps that are undesired are closed.

8. The method of claim 7, the step of contemporaneously adapting one of the upper or lower arch and the upper arch tooth anatomy or lower arch tooth anatomy within the computer software program to maintain an anatomical occlusion including maintaining diastemata or conceding needed space.

9. The method of claim 7 further comprising that the upper arch tooth anatomy or lower arch tooth anatomy comprises more than one tooth.

10. The method of claim 7, the step of contemporaneously adapting one of the upper or lower arch and the upper arch tooth anatomy or lower arch tooth anatomy to maintain an anatomical occlusion further comprising changes in arch shape and size rather than by scaling the upper arch tooth anatomy or lower arch tooth anatomy.

11. The method of claim 7 further comprising morphing teeth in different directions.

12. The method of claim 7, the step of contemporaneously adapting one of the upper or lower arch and the upper arch tooth anatomy or lower arch tooth anatomy within the computer software program to maintain an anatomical occlusion further utilizing canine guidance.

\* \* \* \* \*